US00PP37732P2

(12) United States Plant Patent
Wyckstandt

(10) Patent No.: US PP37,732 P2
(45) Date of Patent: Oct. 6, 2026

(54) ***AGAPANTHUS* PLANT NAMED 'A19002'**

(50) Latin Name: ***Agapanthus* hybrid**
Varietal Denomination: A19002

(71) Applicant: Tim Wyckstandt, Aalter (BE)

(72) Inventor: Tim Wyckstandt, Aalter (BE)

(73) Assignee: VAN VLIET NEW PLANTS B.V., Stroe (NL)

( * ) Notice: Subject to any disclaimer, the term of this patent is extended or adjusted under 35 U.S.C. 154(b) by 0 days.

(21) Appl. No.: 19/422,442

(22) Filed: Dec. 17, 2025

(30) Foreign Application Priority Data

Aug. 19, 2025 (QZ) ..... PBR 20251671

(51) Int. Cl.
*A01H 5/02* (2018.01)
*A01H 6/04* (2018.01)

(52) U.S. Cl.
USPC ..... Plt./398

(58) Field of Classification Search
USPC ..... Plt./263.1, 398
See application file for complete search history.

(56) References Cited

U.S. PATENT DOCUMENTS

PP15,470 P2 * 1/2005 Rigney ..... A01H 5/02
Plt./398

* cited by examiner

*Primary Examiner* — Karen M Redden
(74) *Attorney, Agent, or Firm* — Penny J. Aguirre

(57) ABSTRACT

A new cultivar of *Agapanthus* plant named 'A19002' that is characterized by its long flowering period, its floriferous blooming habit with a high number of flowering stems produced, its flowers that are white in color and non-fading, and its compact plant habit with a height of an average of 60 cm.

3 Drawing Sheets

Botanical classification: *Agapanthus* hybrid.
Varietal denomination: 'A19002'.

CROSS REFERENCE TO RELATED APPLICATIONS

This application claims priority to European Community Plant Variety Office (CPVO) Plant Breeder's Rights Application No. 2025/1671, filed Aug. 19, 2025. The Applicant received the information for the Plant breeders' rights application directly from the Inventor. This application is co-pending with a U.S. Plant Patent Applications filed for a plant patent derived from the same breeding program that is entitled *Agapanthus* Plant Named 'A21001' (U.S. Plant patent application Ser. No. 19/442.443), *Agapanthus* Plant Named 'A22004' (U.S. Plant patent application Ser. No. 19/442,445), *Agapanthus* Plant Named 'Su Casa' (U.S. patent application Ser. No. 19/442,434), and *Agapanthus* Plant Named 'Vitro002' (U.S. Plant patent application Ser. No. 19/442,451).

BACKGROUND OF THE INVENTION

The present invention relates to a new and distinct cultivar of *Agapanthus* of hybrid origin and will be referred to hereafter by its cultivar name, 'A19002'. 'A19002' represents a new perennial grown for landscape and container use.

The new cultivar was derived from a controlled breeding program by the Inventor in Aalter, Belgium. The goal of the breeding program was to develop a new cultivar of *Agapanthus* with white inflorescences, a compact and low growing plant habit, and a long flowering period. The new cultivar arose from open-pollination of *Agapanthus* 'Marijke' (not patented) in July of 2021. The male parent is therefore unknown. 'A19002' was selected as a single unique plant from the resulting 10,000 seedlings evaluated in July of 2022.

Asexual propagation of the new cultivar was first accomplished by division by the Inventor in Aalter, Belgium in September of 2022. Asexual propagation by division and tissue culture utilizing meristematic tissue has determined that the characteristics of the new cultivar are stable and are reproduced true to type in successive generations.

SUMMARY OF THE INVENTION

The following traits have been repeatedly observed and represent the characteristics of the new cultivar. The characteristics in combination distinguish 'A19002' as a distinct cultivar of *Agapanthus*.

1. 'A19002' exhibits a long flowering period.
2. 'A19002' exhibits a floriferous blooming habit with a high number of flowering stems produced.
3. 'A19002' exhibits flowers that are white in color and non-fading.
4. 'A19002' exhibits a compact plant habit with a height of an average of 60 cm.

The female parent of 'A19002' differs from 'A19002' in having violet-blue colored flowers, less flowering stems, and a shorter flowering period. 'A19002' can be most closely compared to the *Agapanthus* cultivars 'AAOPR017' (not patented) and 'WP001' (U.S. Plant Pat. No. 27,357). 'AAOPR017' is similar to 'A19002' in having flowers that are white in color. 'AAOPR017' differs from 'A19002' in having foliage that is more grey-green color, less flowers, and a shorter blooming period. 'WP001' is similar to 'A19002' in having flowers that are white in color and a long blooming period. 'WP001' differs from 'A19002' in having a shorter plant height, lighter green foliage and less healthy, inflorescences that are less open, and larger flowers with filaments that are less dark yellow.

'A19002' can also be compared to the co-pending cultivars of *Agapanthus*; 'A21001', 'A22004', 'Su Casa' and 'Vitro002'. 'A21001' differs from 'A19002' in having deep blue flowers with blue filaments. 'A22004' differs from 'A19002' in having violet-blue flowers with a darker central stripe on the tepals. 'Su Casa' differs from 'A19002' in having light violet-blue flowers. 'Vitro002' differs from 'A19002' in having white flowers with yellow filaments.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the effective filing date. Disclosures include website listings by van Vliet New Plants and Floramedia.

BRIEF DESCRIPTION OF THE DRAWINGS

The accompanying color photographs illustrate the overall appearance and distinct characteristics of the new *Agapanthus*. The photographs were taken of plants 19 months in age of 'A19002' as grown in an unheated poly-covered tunnel in a 19-cm container in Aalter, Belgium.

The photograph in FIG. 1 provides a side view of a plant of 'A19002' in bloom.

Figure 1:
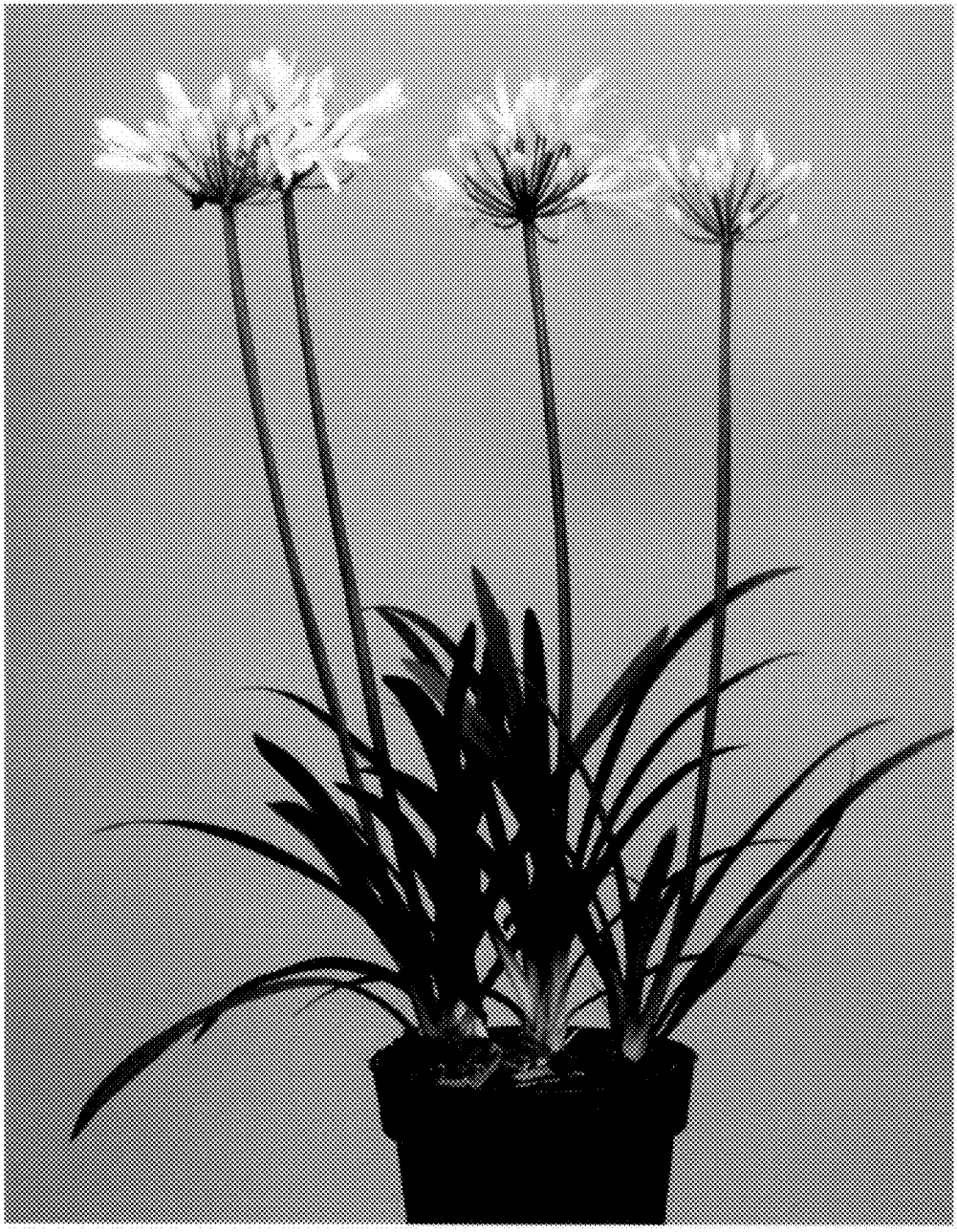
Figure 2:
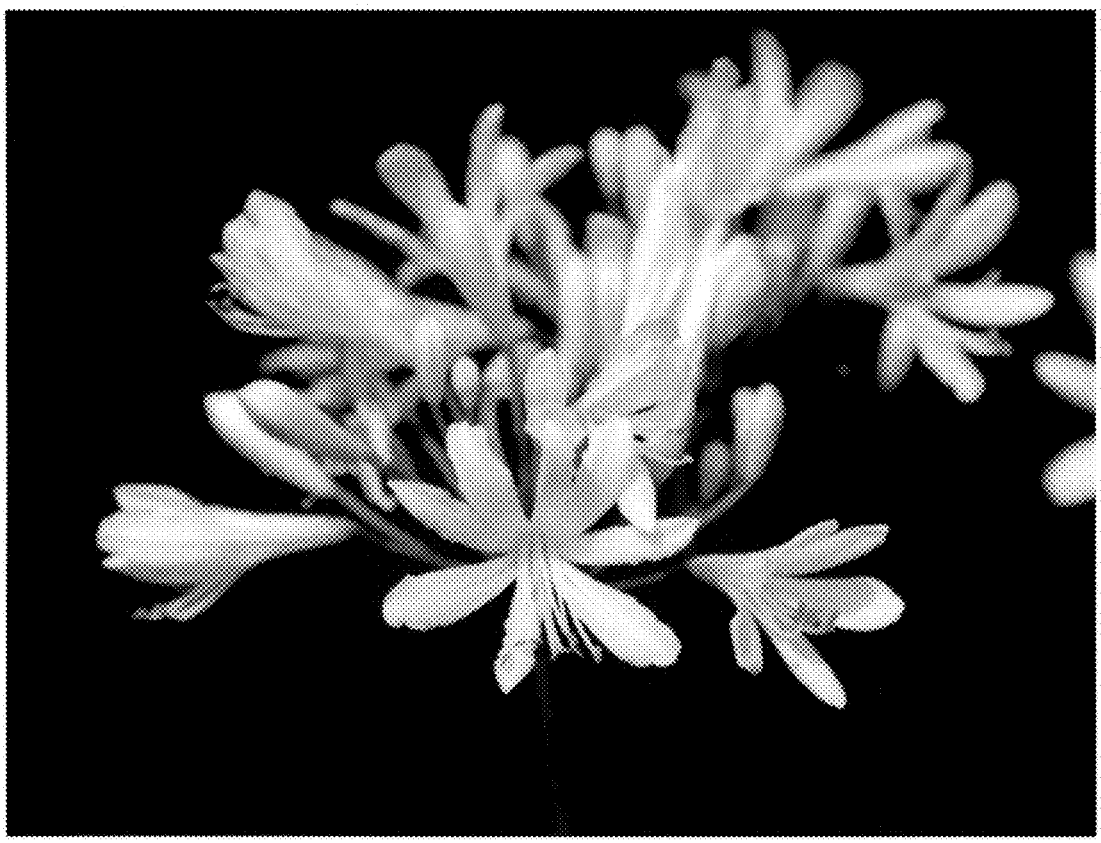

The photograph in FIG. 2 provides a close-up view of an inflorescence of 'A19002'.

Figure 3:
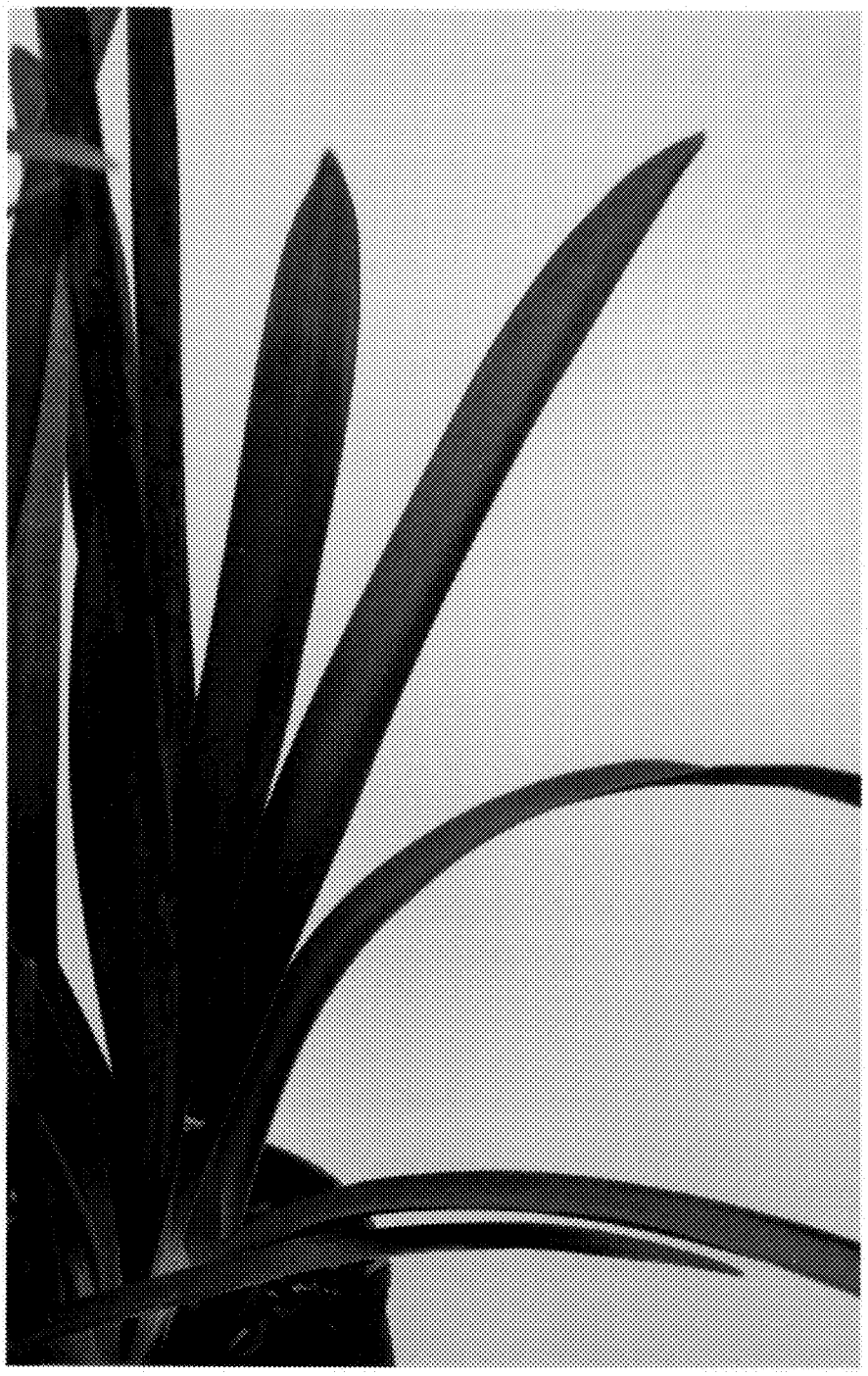

The photograph in FIG. 3 provides a close-up view of the foliage. The photograph in FIG. 3 provides a close-up view of the foliage of 'A19002'.

The colors in the photographs are as close as possible with the photographic and printing technology utilized and color values cited in the detailed botanical description accurately describe the colors of the new *Agapanthus*.

DETAILED BOTANICAL DESCRIPTION

The following is a detailed description of 19-month-old plants of 'A19002' as grown in an unheated poly-covered tunnel in 19-cm containers in Aalter, Belgium. The phenotype of the new cultivar may vary with variations in environmental, climatic, and cultural conditions, as it has not been tested under all possible environmental conditions. The color determinations are in accordance with The 2015 (2019 reprint) Colour Chart of The Royal Horticultural Society, London, England, except where general color terms of ordinary dictionary significance are used.

General description:

*Blooming period*.—Late May to November in Belgium.

*Plant type*.—Semi-deciduous (climate dependent) herbaceous perennial.

*Plant habit*.—Basal rosettes with inflorescences emerging from the rosette center.

*Height and spread*.—An average of 60 cm in height and 50 cm in spread as grown in the landscape.

*Hardiness*.—At least in U.S.D.A. Zones 8 to 12.

*Diseases and pests*.—No resistance or susceptibility to diseases or pest has been observed.

*Root description*.—Thick and fleshy.

*Propagation*.—Division and tissue culture.

Foliage description:

*Leaf shape*.—Ligulate.

*Leaf division*.—Simple.

*Leaf base*.—Decurrent, broadly cuneate.

*Leaf apex*.—Acute.

*Leaf aspect*.—Moderately carinate, slightly to moderately curved.

*Leaf venation*.—Parallel, upper surface; 137B, lower surface; 144D, secondary veins 137A.

*Leaf margins*.—Entire.

*Leaf size*.—Up to 21.5 cm in length and up to 1.7 cm in width.

*Leaf surface*.—Both surfaces non-rugose, upper surface 144A, lower surface a blend of 144A and 146B.

*Leaf number*.—Average of 12 leaves per rosette.

*Foliage density*.—Medium.

*Leaf color*.—Young leaves upper surface; 144A, young leaves lower surface; a blend of 144A and 146B, mature leaves upper surface; 137B, mature leaves lower surface; 138A.

*Leaf attachment*.—Sessile to base.

Flower description:

*Inflorescence type*.—Umbel, hemispherical.

*Flower fragrance*.—None.

*Flower type*.—Rotate, campanulate, base of tepals fused.

*Flower number*.—An average of 25 flowers per umbel, 140 buds and flowers per plant. Inflorescence size.—Average of 8.8 cm in height and 13.8 cm in diameter.

*Flower size*.—An average of 3.4 cm in depth, 4.7 cm in diameter, throat 4 mm in diameter, tube; 1.2 cm in length and 5 mm in diameter.

*Lastingness of inflorescence*.—10 days, self-cleaning.

*Flower aspect*.—Primarily upright from pedicel.

*Peduncle*.—1 per rosette, very sturdy, oval in shape, held primarily upright 72.5° to soil level, surface is glabrous, slightly glaucous and moderately glossy, an average of 45.1 cm in length and 6 mm in diameter, color; a blend of 144A and 146B with thin waxy glaucous layer 193D.

*Pedicels*.—Oval in shape, held in multiple angles, surface is glabrous, glossy, average of 3.7 cm in length and 1.5 mm, 143A in color.

*Flower buds*.—Oblanceolate in shape, matte surface, average of 3.3 cm in length and 9 mm in width, color; NN155B, base tinged 157A, tip 160B.

*Tepals (perianth)*.—6, sometimes 5, rotate, oblanceolate in shape, fused base, entire margins, apex; lower acute, upper bluntly acute, glabrous, slightly velvety, non-rugose, thick substance, 4 cm in length, lower tepal 7.5 mm, upper tepal 1.1 cm, color; when opening and fully open upper surface; NN155D, slightly darker longitudinal central stripe NN155A, when opening lower surface; NN155D, slightly darker longitudinal central stripe NN155A, tip of lower tepals tinged 160C, fully open lower surface;

NN155D, slightly darker longitudinal central stripe NN155A, tip of lower tepals tinged 158C, throat; NN155D, tube; N155A.

*Bracts*.—Immature inflorescence; 1 bract, dropped when individual flowers develop to open, broadly ovate in shape, 3 mm in length, 9 mm in width, color; upper surface 163D, base 157A, apex 159D, lower surface 163C, base 149D and 150C, top 155D, veins on both surfaces 164B, pedicel bract; a single bract at base, filiform in shape, 2.3 cm in length, 0.5 mm in width, color; 158B, tip 164B.

Reproductive organs:

*Gynoecium*.—Pistil; 1, average of 2.1 cm in length, stigma; club-shaped, NN155A in color, style; 2 cm in length, NN155D, ovary; oblong in shape, 1 cm in length, 4 mm in width and 144D and N144D in color, pistil lodes not present.

*Androecium*.—Stamens; 6, anthers; basifixed, oblong in shape, 5 mm in length, 1.5 mm in width, 152C in color, filament; 2.4 cm in length, NN155D in color, pollen; moderate in quantity and 17C in color, staminodes not present.

*Fruit/seed*.—None observed to date.

It is claimed:

1. A new and distinct cultivar of *Agapanthus* plant named 'A19002' as herein illustrated and described.

* * * * *